United States Patent
Frey et al.

(10) Patent No.: US 8,987,527 B2
(45) Date of Patent: Mar. 24, 2015

(54) PROCESS FOR OBTAINING TRIMETHYLOLPROPANE-ENRICHED PRODUCT STREAMS FROM THE SECONDARY STREAMS OF TRIMETHYLOLPROPANE PREPARATION

(71) Applicant: Oxea GmbH, Oberhausen (DE)

(72) Inventors: Guido D. Frey, Riedstadt (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 14/359,118

(22) PCT Filed: Nov. 28, 2012

(86) PCT No.: PCT/EP2012/004904
§ 371 (c)(1),
(2) Date: May 19, 2014

(87) PCT Pub. No.: WO2013/091765
PCT Pub. Date: Jun. 27, 2013

(65) Prior Publication Data
US 2014/0296583 A1 Oct. 2, 2014

(30) Foreign Application Priority Data
Dec. 23, 2011 (DE) .......................... 10 2011 122 356

(51) Int. Cl.
*C07C 29/90* (2006.01)
*C07C 29/80* (2006.01)
*A47L 9/14* (2006.01)

(52) U.S. Cl.
CPC .................. *C07C 29/90* (2013.01); *C07C 29/80* (2013.01); *A47L 9/1481* (2013.01)
USPC ........................................................ 568/854

(58) Field of Classification Search
None
See application file for complete search history.

(56) References Cited

U.S. PATENT DOCUMENTS

| 3,478,115 | A | 11/1969 | Bronstein, Jr. | |
| 5,603,835 | A | 2/1997 | Cheung et al. | |
| 5,948,943 | A | 9/1999 | Supplee et al. | |
| 6,265,623 | B1 | 7/2001 | Morawietz et al. | |
| 6,586,642 | B2 * | 7/2003 | Dernbach et al. | 568/854 |
| 7,057,080 | B2 * | 6/2006 | Dernbach et al. | 568/700 |
| 2013/0131391 | A1 | 5/2013 | Kreickmann et al. | |

FOREIGN PATENT DOCUMENTS

| DE | 1768348 B1 | 12/1971 |
| DE | 19840276 A1 | 3/2000 |
| DE | 10058303 A1 | 5/2002 |
| DE | 102010033844 A1 | 2/2012 |
| DE | 102011118953 A1 | 5/2013 |
| DE | 102011118956 A1 | 5/2013 |
| DE | 102011118993 A1 | 5/2013 |
| EP | 1178030 A2 | 7/2001 |
| GB | 1026425 | 8/1963 |
| WO | 9701523 A1 | 1/1997 |
| WO | 9717313 A1 | 5/1997 |
| WO | 0147850 A2 | 7/2001 |
| WO | 2004013074 A1 | 2/2004 |

OTHER PUBLICATIONS

Database CAPLUS on STN, Acc. No. 1991:448843, Kisan et al., DD 287252 A5 (Feb. 21, 1991) (abstract).*
International Search Report mailed Mar. 6, 2013.

* cited by examiner

*Primary Examiner* — Brian J Davis
(74) *Attorney, Agent, or Firm* — Michael W. Ferrell

(57) ABSTRACT

A process for obtaining trimethylolpropane-enriched product streams from the forerun fractions obtained in the distillative purification of trimethylolpropane is characterized in that: (a) the forerun fractions are treated separately or in combination at a temperature of 160 to 280° C. and at a pressure of 1 to 30 MPa with hydrogen in the presence of a hydrogenation catalyst and an acidic compound; and (b) the reaction mixture obtained after step a) is separated by distillation into a trimethylolpropane-enriched, catalyst-free product stream and a catalyst-containing product stream. The trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds.

20 Claims, No Drawings

PROCESS FOR OBTAINING TRIMETHYLOLPROPANE-ENRICHED PRODUCT STREAMS FROM THE SECONDARY STREAMS OF TRIMETHYLOLPROPANE PREPARATION

CLAIM FOR PRIORITY

This application is a national phase application of PCT/EP2012/004904 FILED Nov. 28, 2012 which was based on application DE 10 2011 122 356.1 FILED Dec. 23, 2011. The priorities of PCT/EP2012/004904 and DE 10 2011 120 356.1 are hereby claimed and their disclosures incorporated herein by reference.

TECHNICAL FIELD

The present invention relates to a process for obtaining trimethylolpropane-enriched product streams from the secondary streams of trimethylolpropane preparation.

BACKGROUND

Trimethylolpropane is a trihydric alcohol which is of significance for the production of coating materials, polyurethanes and polyesters, for example of alkyd resins. Trimethylolpropane is produced industrially by condensation reaction of n-butyraldehyde with formaldehyde according to different variants.

In what is called the hydrogenation process, at least two moles of formaldehyde are added onto one mole of n-butyraldehyde in the presence of a catalytic amount of a tertiary amine via the monomethylolbutyraldehyde intermediate to initially give dimethylolbutyraldehyde, which is then converted to trimethylolpropane in a hydrogenation step. According to the process described in WO98/28253 A1, formaldehyde is used with an up to eight-fold molar excess. The reaction mixture obtained from the aldol addition step is worked up either by distillation or by phase separation. In the distillative workup, unconverted or partly converted starting compounds are drawn off as volatile components and recycled into the reaction stage, while the bottom product is converted further. If, instead of the distillative workup, the reaction mixture is separated in a phase separator into the aqueous and organic phases, the organic phase is returned to the aldol addition and the aqueous phase is processed further. There follows a catalytic and/or thermal treatment in order to convert monomethylolbutyraldehyde to dimethylolbutyraldehyde. By-products formed are removed by distillation and the bottom product of this distillation is subsequently catalytically hydrogenated to obtain trimethylolpropane. The crude trimethylolpropane obtained is subsequently subjected to a purifying distillation. After removal of low and medium boilers, purified trimethylolpropane is obtained as an intermediate fraction, while higher-boiling condensation products within which trimethylolpropane equivalents are bound are obtained as the tailings or bottoms fraction.

In addition to the hydrogenation process, trimethylolpropane is also prepared industrially by what is known as the Cannizzaro reaction. In a first reaction stage, n-butyraldehyde and formaldehyde are reacted with addition of stoichiometric amounts of a base to give dimethylolbutyraldehyde, which is subsequently reduced with excess formaldehyde to give trimethylolpropane, while one equivalent of formate is formed simultaneously. Typically, the base used is an aqueous solution of an alkali metal or alkaline earth metal compound, for example sodium hydroxide, potassium hydroxide or calcium hydroxide. Since one equivalent of alkali metal or alkaline earth metal formate is obtained as a coproduct in the Cannizzaro process, the economic viability of this process variant also depends on the marketing opportunities for this coproduct. The workup of the aqueous reaction solution obtained, which comprises trimethylolpropane, akali metal or alkaline earth metal formate and excess base, is effected generally by extraction. After neutralization of the excess base, the aqueous solution is extracted with an organic solvent, for example with ethyl acetate. The organic phase is separated from the aqueous phase, which comprises the alkali metal or alkaline earth metal formates in dissolved form, and, after removal of the extractant, trimethylolpropane is obtained by distillation. The resulting trimethylolpropane can be subjected to further purification processes. According to U.S. Pat. No. 5,603,835, an aqueous solution is first prepared from resulting trimethylolpropane, and is extracted once again with an organic solvent, for example with methyl tert-butyl ether. Trimethylolpropane is obtained from the resulting aqueous solution with an improved colour number of less than 100 APHA units.

According to the process known from U.S. Pat. No. 5,948,943, the aqueous, crude reaction solution obtained after the Cannizzaro reaction is treated with a suitable organic solvent at such a temperature that only one liquid phase leaves the extraction vessel. In the subsequent cooling outside the extraction vessel, the aqueous phase separates from the organic phase, and trimethylolpropane can be isolated from the aqueous phase with a colour number of less than 100 APHA.

It is likewise known that the Cannizzaro reaction can be performed with an organic base, for example with a tertiary amine. According to the procedure known from WO97/17313 A1, formaldehyde is prepared with n-butyraldehyde in the presence of stoichiometric amounts of a tertiary amine, forming one equivalent of ammonium formate. Subsequently, water, excess tertiary amine and excess formaldehyde are removed from the crude mixture, and the remaining mixture is heated. This dissociates the ammonium formates to the tertiary amine and formic acid, and the tertiary amine and further volatile constituents are removed, resulting in the formation of trimethylolpropane formate. The tertiary amine removed is either recycled into the Cannizzaro stage or used as a catalyst for the transesterification of the trimethylolpropane formate in a downstream reaction with an added lower aliphatic alcohol. The trimethylolpropane released is subsequently isolated from the crude product.

Irrespective of whether the preparation of trimethylolpropane is effected by the hydrogenation process using catalytic amounts of a tertiary amine, by the Cannizzaro process with molar amounts of a tertiary amine and subsequent transesterification of the trimethylolpropane formate formed, or by the Cannizzaro process with molar amounts of alkali metal or alkaline earth metal hydroxides and the extractive removal thereof, the crude trimethylolpropane obtained is subjected to a single or multiple distillative purification, which is effected under reduced pressure due to the high boiling point. According to DE 100 58 303 A1, the distillative workup of the trimethylolpropane is combined with an ion exchanger treatment, in which case either the aldolization output or the hydrogenation output is contacted with a strongly basic ion exchanger before the distillative workup.

DE 1 768 348 B discloses reaction of two different aldehydes, for example acetaldehyde and butyraldehyde, with formaldehyde in an aqueous alkaline medium. The reaction mixture obtained is first neutralized by adding acid, freed of suspended solids and then treated with acidic and basic ion exchangers.

Distillative purification of crude trimethylolpropane gives rise not only to high boilers and residues but also to fractions having a lower boiling point compared to trimethylolpropane. These forerun fractions comprise, as well as low boilers, for example water, methanol or solvents, also certain amounts of trimethylolpropane itself, according to the separation sharpness in the distillative workup. Additionally present in the forerun fraction are derivatives of trimethylolpropane which have formed by preceding reactions with formaldehyde and methanol and have a boiling point which is lower than or comparable to trimethylolpropane.

Among these derivatives, particularly formaldehyde-containing acetals are represented, which are characterized by the structural element —O—CH$_2$—O— and can also be regarded as formals. Among the formals, the following linear and cyclic formals of trimethylolpropane can be described structurally:

Monocyclic formal of trimethylolpropane:

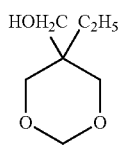

Formula I

Methyl (monolinear) formal of trimethylolpropane:

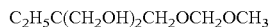

Formula II

Methyl (bislinear) formal of trimethylolpropane:

Formula III

In this context, the monocyclic formal of trimethylolpropane (I) boils at a lower temperature than trimethylolpropane itself. The methanol-derived formals (II) and (III) have a boiling point comparable to trimethylolpropane.

In addition, 2-methylbutanol, 2,2-dimethylpropane-1,3-diol, 2-ethylpropane-1,3-diol and 2-ethyl-2-methylpropane-1,3-diol are present in the forerun fraction.

In the context of the workup of high-boiling fractions and residues obtained in the distillative workup of trimethylolpropane, a number of processes are proposed to dissociate especially formaldehyde-containing acetals and to release trimethylolpropane, in order in this way to improve the yield of the overall trimethylolpropane preparation process. According to WO 2004/013074 A1, the high-boiling fractions and distillation residues obtained in trimethylolpropane preparation are treated with acid, and the water content in the reaction mixture should be 20-90% by weight. It is possible either to obtain trimethylolpropane by distillation from the acid-treated product or to recycle the treated product into the hydrogenation stage of dimethylolbutyraldehyde to give trimethylolpropane. The hydrogenating dissociation of linear or cyclic acetals in aqueous solutions in the presence of a heterogeneous hydrogenation catalyst to give the desired polyhydric alcohol is known from DE 198 40 276 A1. The process requires hydrogenation temperatures above 160° C. in order to suppress the harmful influence of formates, which may still be present particularly in the case of working by the Cannizzaro process, on the hydrogenation performance of the catalyst. According to WO 97/01523 A1, the hydrogenation temperature can be lowered, but a high weight ratio of the catalytically active metal to the cyclic formal then has to be established in order to achieve an acceptable dissociation rate. Moreover, in WO 97/01523 A1 and DE 198 40 276 A1, all working examples are conducted with ruthenium on activated carbon catalysts in order to demonstrate the executability of the processes disclosed. For catalytic dissociation of the formaldehyde-containing acetals, the prior art discloses the use of expensive noble metal catalysts at elevated temperature or use thereof in a comparatively large amount, based on the formaldehyde-containing acetals. The hydrogenating catalytic dissociation can likewise be conducted in the presence of an acid, for example in the presence of a lower carboxylic acid or acidic solids.

SUMMARY OF INVENTION

Since considerable amounts of derivatives with equivalents of trimethylolpropane chemically bound therein are present in the forerun fractions of the distillative workup of trimethylolpropane, it is desirable to release trimethylolpropane from these derivatives and to isolate it together with trimethylolpropane still present in the physical mixture as a trimethylolpropane-rich fraction, which can then be recycled back into the trimethylolpropane purification process, such that the yield of trimethylolpropane over the overall preparation process can be improved. In this way, the forerun fractions obtained in the distillative workup in the course of trimethylolpropane preparation are to be utilized in a very economically viable manner.

The present invention therefore relates to a process for obtaining trimethylolpropane-enriched product streams from the forerun fractions obtained in the distillative purification of trimethylolpropane. It is characterized in that:
(a) the forerun fractions are treated separately or in combination at a temperature of 160 to 280° C. and at a pressure of 1 to 30 MPa with hydrogen in the presence of a hydrogenation catalyst and an acidic compound; and
(b) the reaction mixture obtained after step a) is separated by distillation into a trimethylolpropane-enriched, catalyst-free product stream and a catalyst-containing product stream, wherein trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds.

DETAILED DESCRIPTION

Starting materials for the process according to the invention are streams which are obtained in the distillative purification of trimethylolpropane and have a lower boiling point than trimethylolpropane, and can be referred to as forerun fractions. In general, the forerun fractions are liquid at room temperature.

The individual forerun fractions from the distillative workup of trimethylolpropane can be combined and treated as a starting material by the process according to the invention. According to the distillation conditions, it still comprises trimethylolpropane present in a physical mixture, generally within a range from 2 to 60% by weight, the monocyclic formal of trimethylolpropane (formula I), generally within a range from 2 to 70% by weight, the methyl (monolinear) formal of trimethylolpropane (formula II) and the methyl (bislinear) formal of trimethylolpropane (formula III), generally within a range from 0.5 to 30% by weight, based in each case on the starting material. Further components in the forerun fractions are low boilers such as water or methanol introduced via formaldehyde, 2-methylbutanol, 2,2-dimethylpropane-1,3-diol, 2-ethyl-2-methylpropane-1,3-diol and 2-ethylpropane-1,3-diol, or traces of trimethylolpropane acetals with CAS numbers 58878-16-3, 115392-09-1, 10441-87-9.

Irrespective of whether trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds, the forerun fractions obtained in the distillative purification of trimethylolpropane by the respective preparation process can be worked up by the inventive procedure.

Since the individual forerun fractions having a lower boiling point than trimethylolpropane are liquid at room temperature, the addition of a polar solvent is not absolutely necessary and the forerun fractions can be catalytically hydrogenated separately or in combination, directly and without addition of solvent. However, it is also possible to admix the forerun fractions with a polar solvent separately or in combination. Suitable polar solvents are a lower $C_1$-$C_5$ aliphatic alcohol or $C_2$-$C_{10}$ dialkyl ether, such as methanol, ethanol, propanol or diethyl ether, or especially water. In general, a solution with a content of organic components, neglecting the polar solvent, of 30 to 90% by weight, preferably of 50 to 90% by weight, based on the overall composition, is prepared. Smaller contents of organic components are inappropriate due to the high solvent content. Typically, a solution is produced at room temperature.

The forerun fractions or solutions obtained therefrom are subsequently treated at elevated temperature and elevated pressure with hydrogen in the presence of a hydrogenation catalyst and of an acidic compound. The temperatures employed are in the range from 160 to 280° C., preferably 180 to 230° C., and the pressures employed in the range from 1 to 30 MPa, preferably 5 to 20 MPa. The acidic compounds present may be protic inorganic acids, organic acids or acidic solids. Examples of useful protic inorganic acids include phosphoric acid or sulphuric acid; examples of useful organic acids include lower carboxylic acids such as formic acid, acetic acid, propionic acid or the isomeric butyric acids.

The amount thereof is such that the solution to be subjected to the hydrogenation has a pH in the range from 1 to 5, preferably from 2 to 4.

Due to ease of removability, however, preference is given to working with acidic solids as the acidic compound. Examples of suitable solids of this kind include oxidic compounds such as acidic alumina, natural or silicatic substances such as mordenite, montmorillonite or acidic zeolites, for example those of the Y type, which are available in industrial amounts and are used industrially, for example, in the catalytic cracking of crude oils. The addition thereof is guided by the acidity thereof and, for every 100 parts by weight of solution, they are used generally in an amount of 0.5 to 2 and preferably of 0.5 to 1.0 part by weight; the more acidic the solid, the smaller the amounts used. This generally establishes a pH in the solution of 1 to 6, preferably of 2 to 4.

It is also possible to use commercially available acidic ion exchangers, for example strongly acidic ion exchangers such as Amberlyst 15, Amberlite IR 120, Amberlyst DPT-1, Dowex Marathon-C, Dowex HCR or Lewatit S 100 or Nafion or weakly acidic ion exchangers such as Amberlite ICR 86 or Lewatit CNP. The addition thereof is guided by the acidity thereof, and they are generally used in an amount of 1 to 20 and preferably of 5 to 10 parts by weight, based on 100 parts by weight of solution, and the more acidic the solid the smaller the amounts used.

The catalysts used for the hydrogenation step are customary hydrogenation catalysts, preference being given to heterogeneous hydrogenation catalysts since they can be removed from the reaction mixture in a simple manner, for example by simple filtration in the case of suspension hydrogenation. In the case of fixed bed catalysts too, for example in trickle or liquid phase mode, the reaction mixture can be separated easily from the hydrogenation catalyst.

Typical hydrogenation catalysts comprise, as active components, a noble metal from the group of Ru, Rh, Pd and Pt or a transition metal from the group of Cu, Cr, Co, Ni, Fe, and among these unsupported catalysts such as nickel catalysts, and especially Raney catalysts such as Raney nickel, or chromite catalysts. In addition to unsupported catalysts, supported catalysts are also used; more particularly, suitable support materials for Ru, Rh, Pd or Pt are activated carbon, alumina, $SiO_2$, $TiO_2$, $ZrO_2$ and silicates. The metal loading in the case of supported catalysts is typically in the range from 0.1 to 15%, preferably from 0.5 to 10% and especially from 1 to 5% by weight. It has been found that Ru, Pd and Pt on activated carbon are particularly suitable.

In the case of supported nickel catalysts, nickel as the catalytically active metal is applied generally in an amount of about 5 to 70% by weight, preferably about 10 to about 65% by weight and especially about 20 to 60% by weight, based in each case on the total weight of the catalyst. Suitable catalyst supports include all conventional support materials, for example alumina, alumina hydrates in their various forms, silicon dioxide, polysilicic acids (silica gels) including kieselguhr, silica xerogels, magnesium oxide, zinc oxide, zirconium oxide and activated carbon. As well as the principle nickel and support material components, the catalysts may also comprise additives in minor amounts, which serve, for example, to improve the hydrogenation activity and/or service life and/or selectivity thereof. Such additives are known; examples thereof include the oxides of sodium, potassium, magnesium, calcium, barium, zinc, aluminium, zirconium and chromium. They are added to the catalyst generally in a proportion totalling 0.1 to 50 parts by weight, based on 100 parts by weight of nickel.

The suitability of solid nickel catalysts for the hydrogenation of an aqueous formal-containing solution was unexpected, since it is known, for example, from U.S. Pat. No. 5,210,337 that nickel catalysts can be damaged by presence of formaldehyde in the course of hydrogenation of formals.

The hydrogenation stage is conducted in the presence of the acidic compound, which is present either in dissolved form, for example in the case of added inorganic acids or lower organic carboxylic acids, or as a solid suspended in the solution, continuously or batchwise, for example over fixed bed catalysts in trickle mode or liquid phase mode, and with stirring after the suspension hydrogenation.

In continuous mode, a catalyst hourly space velocity V/Vh, expressed in throughput volume per unit catalyst volume and time, of 0.1 to 1 $h^{-1}$, preferably of 0.2 to 0.5 $h^{-1}$, has been found to be appropriate. In the batchwise process regime, based on 100 parts by weight of input solution neglecting the acidic compound, from 0.1 to 10 and preferably from 0.25 to 5 parts by weight of catalyst are used.

After hydrogenation has ended, the liquid hydrogenated material is worked up by distillation, optionally after neutralization with a base. First of all, in a first distillation unit, the polar solvent, if added before the hydrogenation, and low boilers, especially water and methanol which has formed as a result of hydrogenation of the formaldehyde released in the acetal dissociation, are removed as the tops fraction. For the removal of the polar solvent and of the low boilers, customary distillation units are suitable, such as a distillation column having a boiler and, for example, 2 to 50 theoretical plates, a thin-film evaporator with or without a column attachment, a short-path evaporator or a vaporization vessel, which are typically operated at bottom temperatures of 100 to 180° C. and at standard pressure or appropriately under reduced pressure down to 40 hPa. It is likewise possible to lower the pressure stepwise during the distillation proceeding from standard pressure down to a very low pressure of 3 hPa. The bottoms fraction from the first distillation unit is subsequently introduced to a second distillation unit.

In the second distillation unit, it is possible to obtain, as the tops fraction, a trimethylolpropane-enriched, catalyst-free product stream which may have a purity of trimethylolpropane of more than 96% and which additionally comprises small amounts of intermediate fractions and low boilers. This product stream can be recycled into the purification stage of the overall process for the preparation of trimethylolpropane, appropriately into the purifying distillation stage for obtaining trimethylolpropane. The removal of trimethylolpropane-rich tops fraction is likewise accomplished in a customary distillation unit, such as in a distillation column having a boiler and a suitable number of theoretical plates, in a thin-film evaporator with or without a column attachment, in a short-path evaporator or in a vaporization vessel, which are typically operated at bottom temperatures of 180 to 280° C. and at pressures of 3 to 50 and preferably 10 to 25 hPa. The bottoms fraction removed via the column bottom comprises the catalyst and possibly the acidic compound, especially when hydrogenation is effected in the presence of acidic solids or when, in the case of use of dissolved acidic compounds, the hydrogenation is not followed by neutralization with a base. The catalyst-containing bottoms fraction can, optionally after addition of fresh catalyst and fresh acidic compound, be recycled into the hydrogenation stage a) of the process according to the invention or be used for hydrogenation of high-boiling fractions and residues from trimethylolpropane preparation, for example in the processes according to as yet unpublished German patent application with reference number 10 2011 118 993.2 or 10 2011 118 956.8 for obtaining ditrimethylolpropane and trimethylolpropane-enriched product streams.

In a further configuration of the process according to the invention, the hydrogenation catalyst and further solids, if present, can be separated from the reaction mixture obtained after the hydrogenation step a), for example by filtration. The hydrogenated material which has been freed of the hydrogenation catalyst and any further solids is subsequently worked up by distillation as described above. The present invention therefore likewise relates to a process for obtaining trimethylolpropane-enriched product streams from the forerun fractions obtained in the distillative purification of trimethylolpropane. It is characterized in that:
  (a) the forerun fractions are treated separately or in combination at a temperature of 160 to 280° C. and at a pressure of 1 to 30 MPa with hydrogen in the presence of a hydrogenation catalyst and an acidic compound;
  (b) hydrogenation catalyst and further solids, if present, are separated from the reaction mixture obtained after step a); and
  (c) a trimethylolpropane-enriched product stream is obtained by distillation from the product obtained after step b),
wherein trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds.

If the hydrogenation is performed in the presence of dissolved acidic compounds, it is advisable to neutralize with a base before the hydrogenated material is worked up further. As described above, in a first distillation unit, low boilers are removed as the tops fraction. The resulting bottoms fraction is subsequently introduced to a second distillation unit in which a trimethylolpropane-enriched tops fraction is drawn off. The bottoms fraction removed via the column bottom can subsequently be added to the high-boiling fractions and residues from trimethylolpropane preparation, which can be worked up by the process of the as yet unpublished German patent application 10 2011 118 953.3. The distillation conditions employed in the first and second distillation units corresponds to the conditions which are established in the workup of the catalyst-containing hydrogenated material.

In a further configuration of the process according to the invention, the distillative workup of the hydrogenated material freed of solids may optionally be preceded by a treatment with an ion exchanger, for example either only with a basic or acidic ion exchanger or a combination thereof in any sequence. Operation is effected at customary temperatures in the range from 1 to 100° C., preferably in the range from 20 to 60° C., and standard pressure.

If the hydrogenation was effected in the presence of dissolved inorganic acids or lower organic carboxylic acids, the solution is neutralized by addition of base after removing the hydrogenation catalyst. In this case too, treatment with an ion exchanger may follow, specifically at customary temperatures in the range from 1 to 100° C., preferably in the range from 20 to 60° C., and at standard pressure. The ion exchanger treatment removes not only the salts formed after base addition but additionally also further impurities.

The basic ion exchangers include those containing primary, secondary, tertiary or quaternary amino groups. Particular significance has been gained by polystyrene-based ion exchangers containing tertiary amino groups or quaternary amino groups in base form. Examples of weakly to strongly basic ion exchangers are Amberlit IR 45, Dowex 4 or Dowex Marathon-A. Particular industrial significance has been gained by macroreticular types such as Amberlyst A21, Lewatit MP62, Lewatit MP64, Imac A20, Zerolit G, Amberlit IRA93 or Amberlyst A26.

Weakly or strongly acidic ion exchangers contain, for example, the carboxylate or sulpho group, which are bonded to a polymer matrix based on styrene-divinylbenzene copolymers. The carboxylate group may be derived, for example, from aromatic carboxylic acids or aliphatic carboxylic acids, and the sulpho group from aromatic or aliphatic sulphonic acids. A strongly acidic ion exchanger is, for example, Amberlyst 15, Amberlyst DPT-1 or Dowex Marathon-C.

The solution is contacted with the ion exchanger in a suitable reactor. The ion exchanger may be arranged, for example, in a tubular reactor as a fixed bed through which the solution flows. The fixed bed volume and the size of the ion exchanger particles can be varied within wide ranges and thus matched to the chosen reaction conditions and the process features, such as the desired flow rate. It has been found to be useful to observe space velocities in the range from 1 to 10 and especially from 5 to 8 ($V_{solution}/[V_{ion\ exchanger}\ h]$). These are guide parameters which should appropriately be chosen.

In another embodiment of the inventive procedure, the ion exchanger, which may be very finely divided in this case, is suspended in the solution. It is appropriate to keep the suspension in constant motion, for example by stirring or introducing a gas, for example air or nitrogen, in order to achieve intimate contact between the liquid phase and the ion exchanger. The mass ratio of liquid phase to ion exchanger can be set substantially freely and thus in accordance with the individual requirements. It has been found to be useful, for every 100 parts by weight of solution, to use 1 to 10 and preferably 3 to 8 parts by weight of ion exchanger. For the performance of this process variant, for example, stirred tanks or autoclaves are suitable.

In this procedure, the ion exchanger, however, is subject to mechanical stress, and the conditions for the mixing of liquid phase with the ion exchanger should be adjusted such that abrasion on the surface of the particles or even mechanical damage to the particles is avoided.

The solution can be recirculated in order to complete the removal of impurities by multiple treatment of the liquid phase. It is likewise possible to conduct the adsorption in several stages; it is possible to conduct the reaction either batchwise or continuously. The optional ion exchanger treatment is particularly suitable in the case of workup of an aqueous hydrogenated material.

After the optional ion exchanger treatment of the liquid hydrogenated material, the resulting eluate is worked up by distillation as described above in the two-stage connection of distillation units.

The process according to the invention permits the economically viable utilization of forerun fractions obtained in the distillative purification of trimethylolpropane. The recycling of the trimethylolpropane-rich product streams obtained therefrom into the overall preparation process allows the plant efficiency and the yield of trimethylolpropane to be improved with respect to a process regime in which the forerun fractions from the trimethylolpropane distillation are not worked up and not recycled.

The examples which follow describe the process according to the invention in detail. It is of course not restricted to the embodiment described.

EXAMPLES

Example 1

For the inventive workup of the forerun fractions from the distillative purification of trimethylolpropane, a mixture having the following composition (%) determined by gas chromatography was used:

| | |
|---|---|
| Forerun | 8.4 |
| 2-Methylbutanol | 0 |
| Intermediate fraction I | 0 |
| 2,2-Dimethylpropane-1,3-diol | 1.8 |
| 2-Ethylpropane-1,3-diol | 29.0 |
| 2-Ethyl-2-methylpropane-1,3-diol | 0.1 |
| Monocyclic formal (I) | 22.2 |
| Trimethylolpropane | 17.7 |
| Methyl (monolinear) formal (II) | 20.7 |
| High boilers | 0.1 |

In a 1 litre autoclave, 360 grams of the organic input mixture were mixed with 240 grams of water to give a homogeneous solution. 15 grams of the CBV 600 zeolite from Zeolyst were added, as were 9 grams of the hydrogenation catalyst. In experiment 1, a ruthenium-on-activated carbon catalyst in powder form from Johnson Matthey with a metal loading of 5% by weight was used. According to experiment 2, the commercial PRICAT Ni52/35 nickel catalyst from Johnson Matthey with a nickel loading of 52% by weight was used. The hydrogenation conditions and the gas chromatography analysis of the hydrogenated material are compiled in Table 1.

TABLE 1

Catalytic hydrogenation of an aqueous solution of foreruns from trimethylolpropane distillation in the presence of CBV 600 zeolite

| Reaction conditions | Experiment 1 | Experiment 2 |
|---|---|---|
| Catalyst | Ru-C | Ni 52/35 |
| Temperature (° C.) | 200 | 200 |
| Pressure (MPa) | 8 | 8 |
| Reaction time (h) | 6 | 6 |
| Composition determined by gas chromatography (% organic content, anhydrous) | | |
| Forerun | 12.3 | 10.0 |
| 2-Methylbutanol | 2.6 | 1.9 |
| Intermediate fraction I | 0.1 | 0.0 |
| 2,2-Dimethylpropane-1,3-diol | 2.0 | 2.0 |
| 2-Ethylpropane-1,3-diol | 26.0 | 30.0 |
| 2-Ethyl-2-methylpropane-1,3-diol | 0.6 | 0.3 |
| Monocyclic formal (I) | 0.1 | 0.4 |
| Trimethylolpropane | 55.0 | 52.7 |
| Methyl (monolinear) formal (II) | 1.0 | 2.5 |
| High boilers | 0.3 | 0.2 |

Example 2

The distillative workup of hydrogenated material obtained according to Example 1, conducted after filtration of the catalyst and of the acidic zeolite, shows the following results:

First distillation in a 15-tray column, water/low boiler removal

| | Input | Tops fraction | Residue |
|---|---|---|---|
| Top temperature [° C.] | | | 65-113 |
| Bottom temperature [° C.] | | | 102-175 |
| Pressure [hPa] | | | 1013-3 |
| Mass [g] | 1034.4 | 697.5 | 336.7* |
| Water content [%] | 41.8 | 62.0 | not determined |
| Composition determined by gas chromatography (% organic content, anhydrous) | | | |
| Forerun | 11.0 | 29.7 | 0.8 |
| 2-Methylbutanol | 2.6 | 10.6 | 0.0 |
| Intermediate fraction I | 0.1 | 0.1 | 0.0 |
| 2,2-Dimethylpropane-1,3-diol | 1.9 | 3.7 | 0.0 |
| 2-Ethylpropane-1,3-diol | 27.1 | 52.4 | 0.3 |
| 2-Ethyl-2-methylpropane-1,3-diol | 0.5 | 0.8 | 0.0 |
| Monocyclic formal (I) | 0.3 | 0.5 | 0.0 |
| Trimethylolpropane | 54.3 | 0.1 | 95.4 |
| Methyl (monolinear) formal (II) | 0.2 | 0.0 | 0 |
| High boilers | 2.0 | 2.1 | 3.5 |

*Distillation loss: 1034.4 g − 697.5 g − 336.7 g = 0.2 g

Second distillation of the residue from the water/low boiler removal (first distillation) in a 15-tray column, trimethylolpropane recovery, high boiler removal.

| | Tops fraction | Residue |
|---|---|---|
| Top temperature [° C.] | | 123-135 |
| Bottom temperature [° C.] | | 178-260 |
| Pressure [hPa] | | 3 |
| Mass [g] | 233.7 | 103.0 |
| Composition determined by gas chromatography (% organic content, anhydrous) | | |

-continued

|  | Tops fraction | Residue |
|---|---|---|
| Forerun | 1.1 | 0.1 |
| 2-Methylbutanol | 0.0 | 0.0 |
| Intermediate fraction I | 0.0 | 0.0 |
| 2,2-Dimethylpropane-1,3-diol | 0.0 | 0.0 |
| 2-Ethylpropane-1,3-diol | 0.6 | 0.0 |
| 2-Ethyl-2-methylpropane-1,3-diol | 0.0 | 0.0 |
| Monocyclic formal (I) | 0.0 | 0.0 |
| Trimethylolpropane | 96.3 | 93.4 |
| Methyl (monolinear) formal (II) | 0.0 | 0.0 |
| High boilers | 2.0 | 6.5 |

As the result of the high boiler removal (second distillation) shows, it is possible to obtain a tops fraction with a trimethylolpropane content of more than 96%, which can be recycled back into the workup process in the trimethylolpropane preparation.

The invention claimed is:

1. Process for obtaining trimethylolpropane-enriched product streams from the forerun fractions obtained in the distillative purification of trimethylolpropane, characterized in that:
    (a) the forerun fractions are treated separately or in combination at a temperature of 160 to 280° C. and at a pressure of 1 to 30 MPa with hydrogen in the presence of a hydrogenation catalyst and an acidic compound; and
    (b) the reaction mixture obtained after step a) is separated by distillation into a trimethylolpropane-enriched, catalyst-free product stream and a catalyst-containing product stream,
wherein trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds.

2. Process for obtaining trimethylolpropane-enriched product streams from the forerun fractions obtained in the distillative purification of trimethylolpropane, characterized in that:
    (a) the forerun fractions are treated separately or in combination at a temperature of 160 to 280° C. and at a pressure of 1 to 30 MPa with hydrogen in the presence of a hydrogenation catalyst and an acidic compound;
    (b) hydrogenation catalyst and further solids, if present, are separated from the reaction mixture obtained after step a); and
    (c) a trimethylolpropane-enriched product stream is obtained by distillation from the product obtained after step b),
wherein trimethylolpropane is prepared by the Cannizzaro process using alkali metal or alkaline earth metal compounds or stoichiometric amounts of trialkylamines, or is produced by the hydrogenation process in the presence of catalytic amounts of trialkylamines or alkali metal or alkaline earth metal compounds.

3. Process according to claim 1, characterized in that treatment with hydrogen in step a) is effected at a temperature of 180 to 230° C. and at pressures in the range from 5 to 20 MPa.

4. Process according to claim 1, characterized in that the trimethylolpropane-enriched product streams are obtained by distillation in a first and second distillation unit.

5. Process according to claim 4, characterized in that the trimethylolpropane-enriched product stream is obtained as the tops fraction of the second distillation unit.

6. Process according to claim 1, characterized in that the hydrogenation catalyst used in step a) is a hydrogenation catalyst with the active components Ru, Rh, Pd or Pt, or Cu, Cr, Co, Ni or Fe.

7. Process according to claim 6, characterized in that the hydrogenation catalyst with the active components Ru, Rh, Pd or Pt is a supported catalyst with activated carbon, aluminium oxides, $SiO_2$, $TiO_2$, $ZrO_2$ or silicates as the support material.

8. Process according to claim 6, characterized in that the hydrogenation catalyst with the active component nickel is a supported catalyst containing nickel in an amount of 5 to 70% by weight, based on the total mass of the hydrogenation catalyst.

9. Process according to claim 8, characterized in that the support material used is aluminium oxide, aluminium oxide hydrates, silicon dioxide, polysilicic acid, kieselguhr, silica xerogels, magnesium oxide, zinc oxide, zirconium oxide or activated carbon.

10. Process according to claim 8, characterized in that the supported nickel catalyst additionally comprises oxides of sodium, potassium, magnesium, calcium, barium, zinc, aluminium, zirconium or chromium.

11. Process according to claim 6, characterized in that the hydrogenation catalyst with the active component nickel is an unsupported catalyst.

12. Process according to claim 11, characterized in that the unsupported nickel catalyst is Raney nickel.

13. Process according to claim 2, characterized in that, after step b) and before step c), the product obtained after step b) is treated with an ion exchanger.

14. Process according to claim 13, characterized in that the product obtained after step b) is treated both with a basic and with an acidic ion exchanger in any sequence.

15. Process according to claim 1, characterized in that the forerun fractions are admixed separately or in combination with a polar solvent and the resulting solution is treated with hydrogen according to step a).

16. Process according to claim 15, characterized in that the polar solvent used is a $C_1$-$C_5$ aliphatic alcohol, a $C_2$-$C_{10}$ dialkyl ether or water.

17. Process according to claim 2, characterized in that treatment with hydrogen in step a) is effected at a temperature of 180 to 230° C. and at pressures in the range from 5 to 20 MPa.

18. Process according to claim 2, characterized in that the trimethylolpropane-enriched product streams are obtained by distillation in a first and second distillation unit.

19. Process according to claim 18, characterized in that the trimethylolpropane-enriched product stream is obtained as the tops fraction of the second distillation unit.

20. Process according to claim 2, characterized in that the hydrogenation catalyst used in step a) is a hydrogenation catalyst with the active components Ru, Rh, Pd or Pt, or Cu, Cr, Co, Ni or Fe.

* * * * *